United States Patent [19]
Watts

[11] 3,935,314
[45] Jan. 27, 1976

[54] ANTI-HYPERTENSIVE COMPOSITIONS OF BENZIMIDAZOLE DERIVATIVES

[75] Inventor: Eric Alfred Watts, Harlow, England

[73] Assignee: Beecham Group Limited, England

[22] Filed: Oct. 2, 1974

[21] Appl. No.: 511,227

Related U.S. Application Data
[63] Continuation of Ser. No. 308,719, Nov. 22, 1972, abandoned.

[30] Foreign Application Priority Data
Nov. 24, 1971 United Kingdom............ 54498/71

[52] U.S. Cl. .................................................. 424/273
[51] Int. Cl.² ........................................ A61K 31/415
[58] Field of Search ................................... 424/273

[56] References Cited
UNITED STATES PATENTS

| | | | |
|---|---|---|---|
| 3,738,994 | 6/1973 | Fisher | 423/273 |
| 3,749,734 | 7/1973 | Hannah et al. | 424/273 |
| 3,749,789 | 7/1973 | Fisher | 424/273 |
| 3,755,314 | 8/1973 | Fauran et al. | 424/273 |
| 3,760,081 | 9/1973 | Skaletecky | 424/273 |

*Primary Examiner*—Jerome D. Goldberg

[57] ABSTRACT

Antihypertensive pharmaceutical compositions comprising a compound of the formula (II)

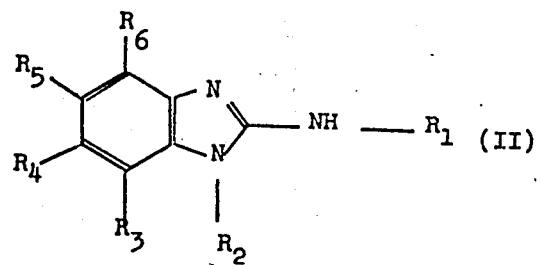

or pharmaceutically acceptable salts or solvates thereof wherein $R_1$ is nitrile or amidino; $R_2$ is hydrogen or lower hydrocarbon; $R_3$, $R_4$, $R_5$ and $R_6$ which may be the same or different, are each selected from hydrogen, halogen, nitro, trifluoromethyl, lower alkyl, lower acyl, hydroxyl, lower etherified hydroxyl or lower acylated hydroxyl; together with a pharmaceutically acceptable carrier. The compounds of formula (II) are also useful as intermediates in the synthesis of the corresponding 2-aminoimidazoline compounds.

14 Claims, No Drawings

ANTI-HYPERTENSIVE COMPOSITIONS OF BENZIMIDAZOLE DERIVATIVES

This application is a continuation of application Ser. No. 308,719, filed Nov. 22, 1972, now abandoned.

The present application relates to derivatives of 2-aminobenzimidazole useful as antihypertensive agents or as intermediates in the synthesis of antihypertensive agents.

Many 2-substituted benzimidazoles are known to have biological activity. Generally such active compounds are used as agents for the control of nematode parasites or the like. However, one group of benzimidazoles were shown in Belgium Pat. No: 768300 to have blood pressure lowering effects in mammals. These compounds included those of formula (I):

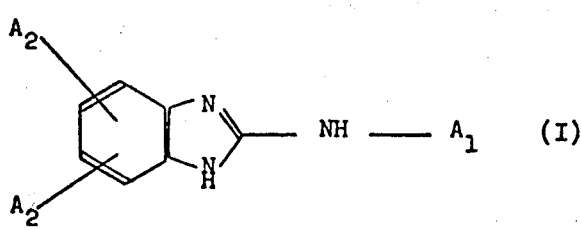

wherein $A_1$ is an acyl group of 2 to 5 carbon atoms and $A_2$ is a hydrogen or halogen atom or a trifluoromethyl, lower alkyl or lower alkoxyl group. From the specification of Belgium Pat. No: 768300 the most active compounds of formula (I) appear to be those wherein $A_1$ is an acetyl group and $A_2$ is a methyl or methoxyl group.

We have now found that when $A_1$ in compounds of formula (I) is replaced by a nitrile or amidino group, the beneficial blood pressure lowering effects may be retained or even enhanced. Furthermore, the resulting compounds may be converted to anti-hypertensive imidazolines as hereinafter described.

Accordingly, the present invention provides a pharmaceutical composition comprising a compound of the formula (II):

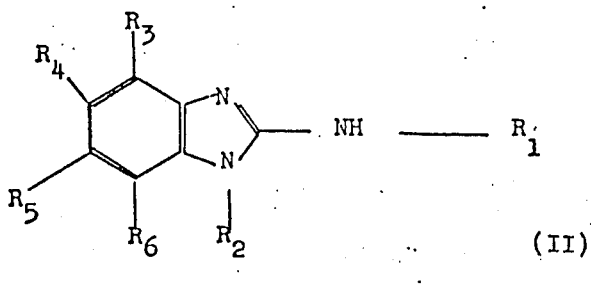

or pharmaceutically acceptable salt or solvate thereof wherein $R_1$ is nitrile or amidino, $R_2$ is a hydrogen atom or a lower hydrocarbon; $R_3$, $R_4$, $R_5$, and $R_6$ which may be the same or different, are each selected from hydrogen, halogen, nitro, trifluoromethyl, lower alkyl, lower acyl, hydroxyl, lower etherified hydroxyl or lower acylated hydroxyl together with a pharmaceutically acceptable carrier.

The term "lower" when used herein means that the group contains from 1 to 7 carbon atoms.

Solvates are generally and preferably hydrates.

The compounds of formula (II) wherein $R_1$ is amidino are nitrogenous bases that form acid addition salts in conventional manner. Such salts include mono- and di-acid addition salts, of acids such as hydrochloric, hydrobromic, hydroiodic, nitric, perchloric, sulphuric, phosphoric, acetic, citric, lactic, tartaric, benzoic, mandelic, sorbic, methanesulphonic, p-toluenesulphinic, salicylic and other conventional inorganic or organic acids.

Compounds of formula (II) wherein $R_1$ is nitrile are acidic and form salts when treated with a base such as an alkali metal hydroxide or other conventional base. Accordingly compounds of formula (II) wherein $R_1$ is nitrile may be present as a metal salt.

Compounds of formula (II) form complexes with metal ions such as $Cu^{2+}$ or transition metal ions known to form complexes with polynitrogenous bases. Such complexes are included within the definition of salts for the purposes of this specification.

The composition of the invention may contain a compound of the formula (I) as the sole pharmaceutically active agent or if desired further pharmaceutically active agents may be present. Suitable further agents include known diuretics, tranquilizers, antihypertensive agents, and other medicaments that are known to show advantage when given to subjects with high blood pressure.

A composition of the invention may be administered orally, parenterally or by suppository, the oral route being preferred.

Typical oral formulations include tablets, pills, capsules, sachets, granules, powders, chewing gum, suspensions, emulsions and solutions; particularly preferred oral formulations are tablets and capsules. Where appropriate and where necessary the formulations may include diluents, binding agents, dispersing agents, surface-active agents, lubricating agents, coating materials, flavouring agents, colouring agents, solvents, thickening agents, suspending agents, sweeteners or any other pharmaceutically acceptable additives, for example gelatin, lactose, starch, talc, magnesium stearate, hydrogenated oils, polyglycols and syrups. Where the formulations are tablets or capsules and the like they will represent pre-measured unit doses or in multi-dose containers from which the appropriate unit dose may be withdrawn.

The injectable form may be aqueous or non-aqueous solution, suspension, or emulsion in a pharmaceutically acceptable liquid (e.g. sterile pyrogen free water or parenterally acceptable oils) or mixtures or liquids which may contain bacteriostatic agents, antioxidants or other preservatives, buffers, (preferably in the physiological pH range of 6.5–7.0), solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn, or as a solid form or concentrate which can be used to quickly prepare an injectable formulation. All formulations for injection are preferably rendered sterile. Suppositories containing the compound will also contain suitable carriers (e.g. coca butter or polyglycols).

Preferably the composition will depend on the strength of the blood pressure lowering effect required and on the age and weight of the subject. Generally, for 70 kg adult, 5 – 5000 mg/day of active agent achieves a suitable effect, 20 – 500 mg/day being preferred. Preferably this dosage is taken in divided form, for example, as from 2 to 5 doses per day, preferably 3 or 4 doses per day. Individual dosage forms may contain from 5 – 500 mgs preferably 10 – 250 mgs.

Especially suitable compositions of the invention containing a compound wherein $R_1$ is a nitrile, are those containing a compound of formula (III):

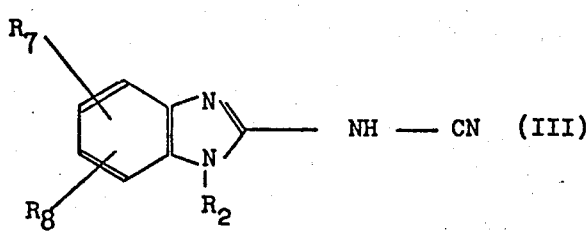

wherein $R_2$ hydrogen or lower hydrocarbon and $R_7$ and $R_8$ are selected from hydrogen, halogen, lower alkyl or lower alkoxyl groups.

Further preferred compounds of formula (III) are those wherein $R_2$ is hydrogen or methyl and $R_7$ and $R_8$ are each hydrogen, chlorine, bromine or methyl.

Especially suitable compositions of the invention containing a compound wherein $R_1$ is an amidino group are those containing a compound of the formula (IV):

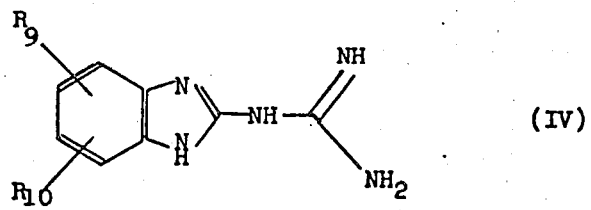

wherein $R_9$ and $R_{10}$ are selected from hydrogen or halogen atoms or lower alkyl or lower alkoxyl groups.

Preferred compounds of formula (IV) include those wherein $R_9$ is hydrogen and $R_{10}$ is hydrogen, chlorine, bromine, methyl, methoxyl, t-butyl or nitro, $R_{10}$ being on the 5-position of the benzimidazole nucleus.

Generally compounds of formula (III) are more active than those of formula (IV).

Certain compounds of formula (II) are novel and accordingly form part of the invention.

Novel benzimidazolyl carbamonitriles of the invention are those of the formula (V):

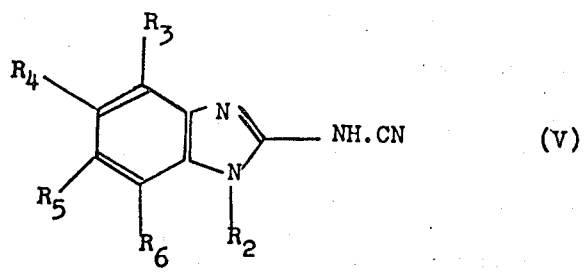

wherein $R_2$ is hydrogen or lower hydrocarbon and at least one of the groups $R_3$, $R_4$, $R_5$ and $R_6$ is halogen or lower alkyl, hydroxyl, lower etherified hydroxyl, nitro lower acylated hydroxyl and the remaining groups $R_2$, $R_3$, $R_4$ and $R_5$ are hydrogen; or a salt or solvate thereof.

Salts are preferably pharmaceutically acceptable salts. Solvates are preferably hydrates. Preferably $R_2$ is hydrogen or methyl.

Suitable groups $R_3$, $R_4$, $R_5$ or $R_6$ may include hydrogen fluorine, bromine, chlorine, nitro, methyl, ethyl, benzyl, t-butyl, hydroxyl, methoxy, ethoxy, benzyloxy, acetoxy, benzoyloxy, or the like.

Preferably 2 or 3 of $R_3$, $R_4$, $R_5$ and $R_6$ are hydrogen atoms and the other group or groups $R_3$, $R_4$, $R_5$ and $R_6$ are chlorine, bromine, hydroxyl, methoxyl, methyl or t-butyl.

An especially preferred group of compounds of formula (V) are those of formula (VI):

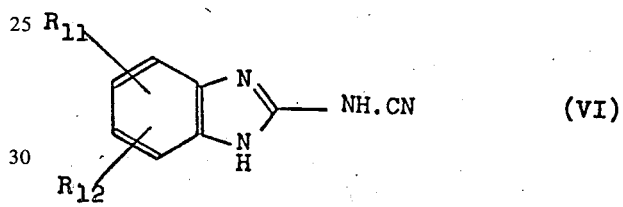

wherein $R_{11}$ is hydrogen, bromine, chlorine, methoxyl or methyl and $R_{12}$ is bromine, chlorine, hydroxyl, methoxyl, methyl or t-butyl.

$R_{11}$ is preferably attached to the 5-position of the benzimidazole ring and $R_{12}$ is preferably attached to the 6-position.

The compounds of formula (V) and in particular the compounds of formulae (VI) and (VIII) will be useful as intermediates in the synthesis of novel aminoimidazolines as hereinafter described.

Particularly useful compounds for such purposes are those of formula (VII):

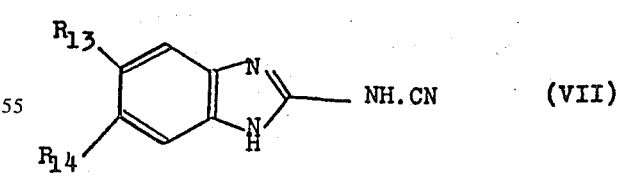

wherein when $R_{13}$ is hydrogen $R_{14}$ is selected from fluorine, chlorine, bromine, methyl, methoxyl, nitro, t-butyl and hydroxyl, and when $R_{13}$ is methyl $R_{14}$ is methyl or chlorine; and when $R_{10}$ is chlorine $R_{11}$ is chlorine.

Compounds of formula (V) may be prepared from corresponding compounds of formula (VIII):

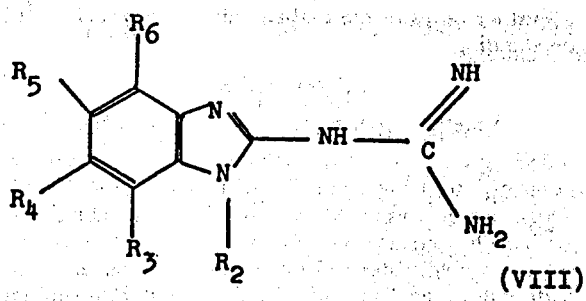

(VIII)

wherein $R_2$, $R_3$, $R_4$, $R_5$ and $R_6$ are as defined with regard to formula (V) except that they do not contain amino groups, by reaction with nitrous acid and thereafter if desired varying substituents $R_3$, $R_4$, $R_5$ and $R_6$ in known manner.

The nitrous acid for this reaction may be preformed or produced in situ by the reaction of an acid and a nitrite salt or ester in known manner, for example, by the reaction of hydrochloric acid and sodium nitrite.

Suitably the reaction will take place in acidic aqueous solution at a depressed temperature, for example, below 10°C, preferably at about 0° – 5°C.

Compounds of formula (II) wherein $R_1$ is amidino may be prepared by the reaction of cyanoguanidine [NC.NH.C(NH)NH$_2$] and an o-diamine (IX)

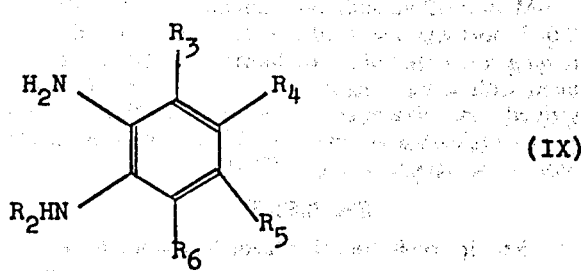

(IX)

and thereafter, if desired, varying the substituents $R_3$, $R_4$, $R_5$ and/or $R_6$ in known manner.

Such a reaction may be carried out at a low, ambient or elevated temperature, for example 0° – 200°C, with non-extreme elevated temperatures being particularly suitable, for example 40° – 120°C, preferably 60° – 110°C.

The reaction is generally carried out in a hydroxylic solvent such as water, aqueous ethanol, isopropanol and the like.

A particularly convenient reaction condition is a refluxing aqueous solution of the o-diamine (IX) and cyanoguanidine in an approximately neutral solution.

The compounds of formula (V) may be converted to further useful anti-hypertensive agents of formula (X):

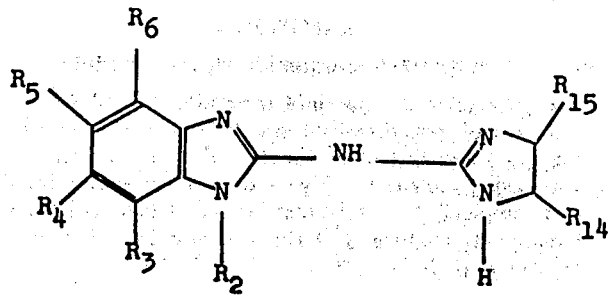

(X)

wherein $R_2$, $R_3$, $R_4$, $R_5$ and $R_6$ and as defined in relation to formula (II) and $R_{14}$ and $R_{15}$ are each hydrogen, methyl or ethyl, by reaction with a diamine (XI):

$$NH_2.CHR_{14}.CHR_{15}.NH_2 \quad (XI)$$

at an elevated temperature, and thereafter if desired varying groups $R_3$, $R_4$, $R_5$, and $R_6$ in known manner.

The following examples serve to illustrate the invention. The structures of the compounds prepared were checked by standard methods of i.r. and n.m.r. and u.v. spectroscopy and elemental analysis. Temperatures are in °C throughout.

EXAMPLE 1

2-guanidino-1-methylbenzimidazole

A mixture of N-methyl-o-phenylenediamine dihydrochloride (10.80g. 0.005 mol) and cyanoguanidine (9.30g, 0.11 mol) was heated under reflux in water (80 ml) for 2½ hours. The reaction mixture was cooled, basified with excess 40% sodium hydroxide, and the resulting precipitate filtered, washed with water and dried in vacuo. (7.19g; m.p. 142°–146°C). This was dissolved in excess dilute hydrochloric acid and evaporated in vacuo. The crude hydrochloride was recrystallised from ethanol/ether to yield 2-guanidino-1-methylbenzimidazole dihydrochloride (600g; 42%) as off-white micro-crystals m.p. 228°–238°C.

A solution of the dihyrochloride in water was basified with excess dilute ammonia to give off-white microcrystals (4.31g). Recrystallisation from benzene/petrol-ether (b.p. 40–60°C) gave 2-guanidino-1-methylbenzimidazole (4.19g) as off-white microcrystals m.p. 178°–179°C.

EXAMPLE 2

1-benzyl-2-guanidinobenzimidazole

N-Benzyl-o-phenylenediamine (12.90g, 0.065 mol) and cyanoguanidine (6.0g, 0.071 mol) were heated under reflux in dilute 5N hydrochloric acid (26.0ml, 0.13 mol) for 6 hours. The reaction mixture was basified with excess 40% sodium hydroxide and extracted with ethyl acetate. The combined extracts were evaporated in vacuo to yield a semi-solid mixture (17.68g). This mixture was separated by elution from Kieselgel with ethyl acetate to give off-white microcrystals which were recrystallised from aqueous methanol to give 1-benzyl-2-guanidinobenzimidazole (4.45g; 26%) as light-brown needles m.p. 167°C.

EXAMPLE 3

2-guanidino-5-nitrobenzimidazole

A mixture of 4-nitro-o-phenylenediamine (15.3g 0.1 mol), cyanoguanidine (9.25g 0.11 mol) and dilute hydrochloric acid (40 ml, 0.2 mol) was heated under reflux for 1½ hours. The reaction mixture was cooled, basified with dilute sodium hydroxide, and filtered. The resulting solid was washed well with water (ca 500 ml), dried in vacuo and boiled with ethanol to yield 2-guanidino-5-nitrobenzimidazole (3.90g; 20%) as pale yellow microcrystals m.p. 305°–307°C.

EXAMPLE 4

2-guanidino-4-methylbenzimidazole

A mixture of 2,3-toluenediamine (12.45g, 0.102 mol)(5N HCl 40. 8ml, 0.204 mol) and cyanoguanidine (8.60g, 0.102 mol) was heated on a steam bath for 1 hour. The hot solution was then basified with 40% sodium hydroxide and allowed to cool. The resulting gummy material which separated was extracted into ether. The combined ether extracts were dried ($Na_2SO_4$) and treated with ethereal hydrogen chloride to give a pink precipitate (25.55g) m.p. 213°–222°C. This crude product was recrystallised from ethanol/ether. A first crop (14.90g), m.p. 236°–238°C. which contained some unreacted 2,2-toluenediamine was obtained but a second crop (5.00g) of colourless microcrystals m.p. 249°–250°C crystallised as pure 2-guanidino-4-methylbenzimidazole dihydrochloride monohydrate.

EXAMPLE 5

4,5-dimethyl-2-guanidinobenzimidazole 3,4-Diamino-o-xylene (6.80g 0.05 mol) and cyanoguanidine (4.20g 0.05 mol) were refluxed together for 2 hours in 5N hydrochloric acid (20 ml). The hot reaction mixture was basified with excess 40% sodium hydroxide and the resulting precipitate filtered, washed with water and dried. Recrystallisation from aqueous ethanol gave 4,5-dimethyl-2-guanidinobenzimidazole (3.89 g, 38%) as pale brown microcrystals m.p. 122°–124°C.

The free base (0.5 g) was dissolved in ethanol and treated with ethereal hydrogen chloride to yield 4,5-dimethyl-2-guanidinobenzimidazole dihydrochloride hemihydrate (0.53 g) as colourless microcrystals m.p. 270–272°C.

EXAMPLE 6

Sodium salt of 2-benzimidazolylcarbamonitrile

2-Benzimidazolylcarbamonitrile (2.29 g 0.0145 mol) [prepared as described by G. Pellizzari, Gazz. Chim. Ital., 51, 140 (1921)] was treated with sodium hydroxide (0.58 g, 0.0145 mol) in water (30 ml) and evaporated in vacuo. The resulting solid was recrystallised from n-propanol/petrolether (b.p. 40°–60°C) to yield 2-benzimidazolylcarbamonitrile as hydrated sodium salt (2.64g) as colourless microcrystals m.p. 320°–321°C.

EXAMPLE 7

1-methyl-2-benzimidazolylcarbamonitrile

2-Guanidino-1-methylbenzimidazole (2.50g. 0.0134 mol) was dissolved in cold water (50 ml) containing concentrated hydrochloric acid (5 ml). The solution was cooled to 0° to 5°C and treated portionwise with sodium nitrite (1.0g). The solution was stirred occasionally and left in the cold for 1 hour during which time the colour lightens and nitrogen was evolved. A further portion of sodium nitrate (0.50g, was then added and 1-methyl-2-benzimidazolylcarbamonitrile (0.085g; 37%) separated as colourless microcrystals m.p. 227°–228°C.

Further crops of the carbamonitrile are precipitated on standing.

EXAMPLE 8

5-methyl-2-benzimidazolylcarbamonitrile

2-Guanidino-5-methylbenzimidazole [prepared as described by King et al, J.Chem. Soc., 1366 (1948, which paper discloses various other guanidinobenzimidazole derivatives] (5.60g 0.0296 mol) was dissolved in cold water (55 ml) containing concentrated hydrochloric acid (10.50 ml). Treatment with sodium nitrite (3.15g) and work up as described in Example 7 gave 5-methyl-2-benzimidazolylcarbamonitrile (4.26 g; 84%) as light brown microcrystals m.p. 340°C.

EXAMPLE 9

5-chloro-2-benzimidazolylcarbamonitrile

5-Chloro-2-guanidinobenzimidazole dihydrochloride (2.35 g, 0.0081 mol) was dissolved in cold water (100 ml) containing concentrated hydrochloric acid (15.0 ml). Treatment with sodium nitrite (3.0 g) and work up described in Example 7 gave 5-chloro-2-benzimidazolylcarbamonitrile (1.12 g; 76%) as colourless microcrystals m.p, shrinking from 278°C (ex aqueous methanol).

EXAMPLE 10

5-methoxy-2-benzimidazolylcarbamonitrile

5-Methoxy-2-guanidinobenzimidazole (17.00 g; 0.083 mol) was dissolved in cold water (350 ml) containing concentrated hydrochloric acid (16 ml). Treatment with sodium nitrite (32 g) and work up as described in Example 7 gave 5-methoxy-2-benzimidazolylcarbamonitrile (10.27 g; 66%) as crude brown microcrystals. m.p. 237°–239°C.

EXAMPLE 11

5,6-dimethyl-2-benzimidazolylcarbamonitrile 5,6-Dimethyl-2-guanidinobenzimidazole (29.0 g 0.143 mol) was dissolved in cold water (2L) containing concentrated hydrochloric acid (50 ml). Treatment with sodium nitrite (20 g) and work up as described in Example 7 gave 5,6-dimethyl-2-benzimidazolylcarbamonitrile (23.66 g; 88%) as pale brown microcrystals m.p. 360°C (ex methanol).

EXAMPLE 12

4-methyl-2-benzimidazolylcarbamonitrile

2-Guanidino-4-methylbenzimidazole dihydrochloride (18.15 g, 0.069 mol) was dissolved in water (700 ml) containing concentrated hydrochloric acid (7.4 ml). Treatment with sodium nitrite (9.8 g) and work up as described in Example 7 gave 4-methyl-2-benzimidazolylcarbamonitrile 6.25g. 53%) as colourless microcrystals m.p. 277°–278°C (ex ethanol).

EXAMPLE 13

4,5-dimethyl-2-benzimidazolylcarbamonitrile 4,5-Dimethyl-2-guanidinobenzimidazole (3.30 g, 0.0159 mol) was dissolved in cold water (35 ml) containing 5N hydrochloric acid (10.8 ml). Treatment with sodium nitrite (2.57 g) and work up as described in Example 7 gave 4,5-dimethyl-2-benzimidazolylcarbamonitrile (0.39 g, 14%) as cream-coloured microcrystals m.p. 247–249°C.

EXAMPLE 14

2-benzimidazolylamino-2'-imidazoline

2-Benzimidazolecarbamonitrile (25.0g, 0.158 mol) and ethylenediamine (28.20g, 0.474 i.e. 3 times excess) were heated under reflux in amyl alcohol (200 ml) for 3 hours. The reaction mixture was cooled and the resulting solid filtered washed with a little cold amyl alcohol to yield 2-benzimidazolylamino-2'-imidazoline as colourless microcrystals. (12.85g 41%) m.p. 254°–256°C. The mother liquors were heated under reflux for a further 2 hours then cooled. The cooled solution was evaporated under reduced pressure. The resulting semi-solid was tritutrated with cold amyl alcohol and the solid filtered to yield a further amount of product. (2.92g 9%).

The above free base (10.84g) was dissolved in slight excess dilute hydrochloric acid and evaporated under reduced pressure. The resulting solid was recrystallised from ethanol/ether to yield 2-benzimidazolylamino-2'-imidazoline dihydrochloride (9.96g) as colourless microcrystals m.p. 262°–264°C.

EXAMPLE 15

2-benzimidazolylamino-2'-imidazoline

2-Guanidinobenzimidazole (2.50g 0.0143 mol) and ethylenediamine (2.64 g 0.0429 mol) were heated under reflux for 90 hours, in amyl alcohol (50 ml). The cooled reaction mixture was evaporated under reduced pressure. The resulting oil was crystallised with a little warm amyl alcohol and the crystalline solid filtered, washed with a little cold amyl alcohol and dried in vacuo to yield 2-benzimidazolylamino-2'-imidazoline (0.73g, 25%) m.p. 254°–256°C identical to that prepared via the carbamonitrile as described in Example 14.

EXAMPLE 16

2-(1-methyl-2-benzimidazolyl)amino-2-imidazoline 1-methyl-2-benzimidazolylcarbamonitrile (1.80g, 0.0105 mol) was heated under reflux with excess anhydrous ethylene diamine (5 ml) in amyl alcohol (15 ml) for 24 hours. The solution was evaporated in vacuo and the resulting oil triturated with a little amyl alcohol. The crystalline precipitate (1.24g) was filtered and dried in vacuo. The crude product was dissolved in excess dilute hydrochloric acid and evaporated in vacuo. The resulting solid was recrystallised twice from ethanol/ether to give 2'-(1-methyl-2-benzimidazolyl)amino-2'-imidazoline hydrochloride (0.65g 22%) as pale brown microcrystals m.p. 306°C decomp.

EXAMPLE 17

2-(4-methyl-2-benzimidazolyl)amino-2'-imidazoline

4-Methylbenzimidazole-2-carbamonitrile (467g, 0.0272 mol) and ethylenediamine (4.90g, 0.0816 mol) were heated under reflux in amyl alcohol (100 ml) for 4 hours. The cooled solution was evaporated to dryness under reduced pressure. The residual gum was triturated with ether, the ether decanted and the residual gum dissolved in ethanol. Treatment of this ethanolic solution with ethereal hydrogen chloride gave a colourless precipitate (6.58 g) m.p. 204°–206°C. Recrystallisation from ethanol/ether gave 2-(4-methyl-2-benzimidazolyl)amino-2-imidazoline dihydrochloride as colourless microcrystals (5.28 g) m.p. 218°–225°C.

The dihydrochloride salt was dissolved in water and the solution basified with 40% sodium hydroxide solution to give a discoloured precipitate, which was filtered and washed with water. Recrystallisation from benzene yielded the free base as buff microcrystals m.p. 230°–240°C.

EXAMPLE 18

2-(5-bromobenzimidazolyl)amino-2'-imidazoline 2-(Benzimidazolyl)amino-2'-imidazoline (2.01 g, 0.01 mol) was dissolved in glacial acetic acid (15 ml) containing a crystal of ferric chloride. The stirred solution was cooled in an ice bath and 6.3% w/v solution of bromine in acetic acid (26 ml) (equivalent to 0.01 mol $Br_2$) was added dropwise over 15 minutes. At the end of the addition, the solution was stirred for a further 15 minutes then basified with 40% sodium hydroxide solution. The resulting precipitate (2.43g; m.p. 264°–266°C) was filtered and washed with water. Recrystallisation from aqueous dimethylformamide gave 2-(5-bromobenzimidazolyl)amino 2-imidazoline (1.19g) as colourless microcrystals m.p. 277°–279°C.

The free base was dissolved in 5N hydrochloric acid and the solution evaporated to dryness under reduced pressure to give the dihydrochloride as colourless microcrystals m.p. 234°–236°C (ex ethanol/ether).

EXAMPLE 19

2-(2-imidazolinylamino)benzimidazole-5-sulphonic acid 2-(Benzimidazolylamino-2-imidazoline (5.00g) was treated cautiously with oleum (20 ml). The resulting solution was stirred and heated at 100°C for 1½ hours. After cooling the solution was poured into ice/water (500 ml). Solid calcium carbonate was then added until the pH was 6.5. The white suspension was brought to the boil and the calcium sulphate filtered from the hot solution. The filtrate was concentrated under reduced pressure, brought to the boil again and filtered to remove a trace of insoluble material. The filtrate was acidified with glacial acetic acid and allowed to stand. A crystalline solid (3.98 g) separated on cooling. Recrystallisation from boiling water gave 2-(2-Imidazoline-2-ylamino)benzimidazole-5-sulphonic acid (1.16g) as colourless microcrystals. m.p. >360°C.

EXAMPLE 20

2-(5-chlorobenzimidazolyl)amino-2-imidazoline

5-Chloro-2-benzimidazolylcarbamonitrile (4.50g, 0.0234 mol) and excess ethylene diamine (4.20g, 0.0702 mol) were heated under reflux in amyl alcohol (25 ml) for 4 hours. The cooled reaction mixture was evaporated under reduced pressure and the residual oil triturated with warm amyl alcohol (10 ml). On standing a buff precipitate crystallises which was filtered washed with a little cold amyl alcohol and dried in vacuo to give 2-(5-Chlorobenzimidazolyl) amino-2-imidazoline (2.70g; 49%) m.p. 287°–289°C.

The free base was dissolved in ethanol, filtered to remove traces of insoluble material and treated with ethereal hydrogen chloride to yield the dihydrochloride (2.47g) as colourless microcrystals m.p. 241°–242°C (ex ethanol/ether).

EXAMPLE 21

2-(5-methylbenzimidazolyl)amino-2'-imidazoline

5-Methyl-2-benzimidazolylcarbamonitrile (3.00g, 0.0165 mol) and ethylene diamine (5.00g, 0.0825 mol) were heated under reflux for 4 hours. The cooled reaction mixture was evaporated under reduced pressure and the residual semisolid crystallised from amyl alcohol (10 mls). The brown crystals were filtered, washed with a little cold amyl alcohol and dried in vacuo to yield 2-(5-Methylbenzimidazolyl)amino-2-imidazoline (1.75g; 50%) m.p. 264°–266°C.

The free base was dissolved in a slight excess of 5N hydrochloric acid, evaporated to dryness under reduced pressure and finally recrystallised twice from ethanol/ether to yield the dihydrochloride as colourless microcrystals m.p. 214°–215°C (after drying at 120°C for 5 hours in vacuo).

EXAMPLE 22

2-(5-methoxybenzimidazolyl)amino-2'-imidazoline

5-Methoxy-2-benzimidazolylcarbamanitrile (1.88g 0.01 mol) and ethylenediamine (4 ml) were heated under reflux in amyl alcohol (45 ml) for 4 hours. The reaction mixture was evaporated under reduced pressure and the resulting oil crystallised from a little amyl alcohol (5 ml) to yield 2-(5-methoxybenzimidazolyl)amino-2-imidazoline (0.90 g; 39%) as colourless microcrystals m.p. 234°–237°C.

This free was dissolved in a slight excess of 5N hydrochloric acid, evaporated to dryness under reduced pressure and recrystallised twice from ethanol/ether to yield the dihydrochloride (0.65g; 21%) as colourless microcrystals m.p. 205°–207°C.

EXAMPLE 23

2-(1-benzylbenzimidazolyl)amino-2-imidazoline 2-(1-Benzylbenzimidazolyl)guanidine (3.65g, 0.0143 mol) was dissolved in water (600 ml) containing 5N hydrochloric acid (5.5 ml). The solution was cooled to 0° to 5°C and treated portionwise with sodium nitrite (1.0g) each hour for 3 hours. After a further 4 hours the reaction mixture was filtered and the microcrystals so obtained were heated under reflux in amyl alcohol (15 ml) with ethylenediamine (3 ml) for 6 hours. The cooled reaction mixture was evaporated to dryness. The resulting semi-solid was crystallised from amyl alcohol was then recrystallised from ethanol to yield 2-(1-benzylbenzimidazolyl)amino-2-imidazoline (1.0g) as colourless microcrystals m.p. 165°–166°C.

EXAMPLE 24

2-(5-nitrobenzimidazolyl)amino-2-imidazoline

2-Benzimidazolylamino-2-imidazoline (10.96g 0.055 mol) was added cautiously to concentrated sulphuric acid (62 ml) cooled to −5°C. Potassium nitrate (5.5 g) in concentrated sulphuric acid (3.4 ml) was added dropwise with stirring maintaining the temperature at 0°C. After addition the reaction mixture was allowed to warm to room temperature overnight then poured onto ice/water (250g) with stirring. The resulting pale yellow crystals were filtered, washed with water and recrystallised from aqueous dimethylforamide to yield 2-(5-nitrobenzimidazolinyl)amino-2-imidazoline trihydrate (15.81g) as yellow microcrystals m.p. 257°–259°C.

EXAMPLE 25

2-(5-aminobenzimidazolyl)amino-2-imidazoline 2-(5-Nitrobenzimidazolyl)amino-2-imidazoline (2.46 g) 5% aqueous methanol (40 ml) and 40% sodium hydroxide (10 ml) were mixed and heated to reflux on a water-bath. A freshly prepared saturated solution of sodium dithionite (200 ml) was added dropwise until the reaction mixture became colourless. The excess methanol was removed under reduced pressure, basified to pH = 14 with sodium hydroxide solution and exhaustively extracted with ethyl acetate. The combined organic extracts were dried over magnesium sulphate filtered and evaporated under reduced pressure to yield 2-(5-Aminobenzimidazolyl)amino-2'-imidazoline (1.28g; 59%) as light brown microcrystals m.p. 285°C.

The free base was dissolved in dilute hydrochloric acid, filtered and evaporated to dryness under reduced pressure. The resulting solid was recrystallised from ethanol/ether to yield the dihydrochloride as off-white microcrystals m.p. 282°–284°C.

EXAMPLE 26

2-(5-aminobenzimidazolyl)amino-2-imidazoline 2-(5-Nitrobenzimidazolyl)amino-2-imidazoline (12.80 g,) was dissolved in anhydrous dimethylformamide (200 ml) and hydrogenated at 50 psi and room temperature for 48 hours, over 5% palladium charcoal (500mgs). The filtered reaction mixture was evaporated under reduced pressure to yield 2-(5-aminobenzimidazolyl)amino-2-imidazoline (9.87g), characterised as the dihydrochloride (7.60g) (m.p. 285°C).

The free base (m.p. 285°C) was obtained by basifying with sodium hydroxide solution and exhaustively extracting with ethylacetate.

EXAMPLE 27

2-(5-hydroxybenzimidazolyl)amino-2-imidazoline 2-(5-Methoxybenzimidazolyl)amino-2-imidazoline (prepared as described in Example 22 (2.55 g 0.011 mol) acetic anhydride (60 ml) and hydrogenbromide (48%) (50 ml) were heated under reflux for 4 hours. The mixture was cooled, evaporated under reduced pressure. The resulting sticky solid was dissolved in water and the filtered solution neutralised with sodium bicarbonate. This aqueous solution was extracted with ethyl acetate. The combined extracts were evaporated under reduced pressure to yield a light brown solid (0.87g) m.p. 254°–258°C. Recrystallisation from methanol gave a low recovery of 2-(5-hydroxybenzimidazolyl)amino-2-imidazoline monohydrate (0.16 g) as pale brown microcrystals m.p. 319°C (decomp.).

EXAMPLE 28

2-(5-hydroxybenzimidazolyl)amino-2-imidazoline 2-(5-Aminobenzimidazolyl)amino-2-imidazoline (2.50 g 0.0116 mol) was dissolved in a cold mixture of concentrated sulphuric acid/water (50 ml of a 40:30 mixture) and diazotised with a cold solution of sodium nitrite in water (a quantity 10% in excess used). A spatula of urea was added when all the sodium nitrite had been added.

The remaining sulphuric acid (210 ml) was heated to 130°–140°C and the diazonium reaction mixture added slowly over a period of 10 minutes. The temperature was allowed to rise to 170°–180°C until small samples failed to show a purple colour when added to an ammoniacal solution of β-napthol. The reaction mixture was poured into an equal volume of cold water then neutralised to pH = 6 using a large volume of 40% sodium hydroxide. The mixture was evaporated under reduced pressure to a small volume (ca 150 ml) and extracted with ethyl acetate. The combined organic extracts were dried over magnesium sulphate filtered and evaporated in vacuo to yield impure 2-(5-hydroxybenzimidazolylamino-2-imidazoline (0.92 g 37%).

EXAMPLE 29

2-(5-hydroxybenzimidazolyl)amino-2-imidazoline

2-Benzimidazolylamino-2-imidazoline (2.50 g 0.01 mol) was dissolved in trifluoroacetic acid (25 ml). Thallium trifluoroacetate (4.50 g, a slight excess) in trifluoroacetic acid (25 ml) was added at room temperature and the mixture allowed to stand overnight at room temperature. The reaction mixture was treated with approx. one equivalent of lead tetracetate in trifluoroacetic acid and the mixture stirred at room temperature for 10–25 minutes. One equivalent of triphenyl phosphine was added and the excess trifluoroacetic acid removed by evaporation under reduced pressure to yield a brown semi-solid. Hydrochloric acid (6 N) was added which precipitated $Pb_{II}$ and $Tl_I$ chlorides. The suspension was then filtered through Kieselguhr and evaporated under reduced pressure to yield a brown solid (3.05 g). This solid was warmed with dilute 10% sodium hydroxide (40 ml) acidified with dilute hydrochloric acid and finally neutralised with sodium bicarbonate. This aqueous solution was extracted with ethyl acetate. The combined organic extracts were dried over magnesium sulphate filtered and evaporated in vacuo to yield a pale green solid mixture (0.52 g). Extraction with sodium hydroxide, acidification of the combined based extract and re-extraction with ethyl acetate yielded 2-(5-hydroxybenzimidazolyl)amino-2-imidiazoline as pale green microcrystals (0.10 g) m.p. 320°C.

EXAMPLE 30

2-(5,6-dichlorobenzimidazolyl)amino-2-imidazoline 2-(Benzimidazolyl)amino-2-imidazoline dihydrochloride (prepared as described in Example 14) (27.4 g, 0.10 mol) was dissolved in concentrated hydrochloric acid (300 ml). The solution was stirred and heated to 80°C. A 15% solution of hydrogen peroxide (68 ml) was added dropwise to the stirred solution maintaining the temperature at 80°C. A colourless crystalline precipitate was soon deposited. At the end of the addition the solution was filtered, whilst hot and the precipitate washed with water and dried. This first crop (22.8 g), m.p. 275°–285°C, was found to be a mixture of chlorinated products. The second crop of crystals was deposited from the filtrate on cooling and was collected, washed with water and dried. This second crop (4.26g), m.p. 278°–281°C was found to be substantially pure 5,6-dichlorinated product. The first crop was recrystallised from aqueous dimethylformamide. The first (2.28 g), m.p. 297°–298°C, and second (6.42 g) m.p. 282°C crops of this recrystallisation were discarded, but the third crop (11.60 g) m.p. 252°–262°C was found to mainly 5,6-dichlorinated material. Both crops of 5,6-dichlorinated product were combined and recrystallised from boiling water to give 2-(5,6-dichlorobenzimidazolyl-2-imidazoline monohydrochloride (9.83 g; 29%) as colourless microcrystals m.p. 279°–281°C.

EXAMPLE 31

2-(4,5,6-trichlorobenzimidazolyl)amino-2-imidazoline

In an identical experiment to that of Example 31 during addition of the hydrogen peroxide solution the temperature rose to 100°C. Fractional crystallisation of a complex mixture of chlorinated products gave a lower yield of 2-(4,5,6-trichlorobenzimidazolyl)amino-2-imidazoline as the free base, m.p. 324°–326°C, in addition to the already characterised 2-(5,6-dichlorobenzimidazolyl)amino-2-imidazoline monohydrochloride m.p. 279°–281°C.

EXAMPLE 32

2-(5,6-dibromobenzimidazolyl)amino-2-imidazoline

2-Benzimidazolylamino-2-imidazoline (2.01 g, 0.01 mol) was dissolved in acetic acid (15 ml) containing a crystal of ferric chloride. The stirred solution was cooled in an ice-bath and a 6.3% w/v solution of bromine in acetic acid (52 ml, equivalent to 0.02 mol $Br_2$) was added in one portion. The resulting solution was stirred for a further 10 minutes to produce a yellow precipitate. The ice-bath was removed; the mixture diluted with water and brought to the boil causing the precipitate to redissolve. The clear solution was basified, whilst hot, with 40% sodium hydroxide. The resulting grey precipitate (3.15 g) was filtered, washed with water and dried in vacuo. Recrystallisation from aqueous dimethylformamide gave 2-(5,6-dibromobenzimidazolyl)amino-2-imidazoline (2.48 g) as colourless microcrystals m.p. 261°–267°C.

The free base was dissolved in a mixture of 5N hydrochloric acid and dimethylformamide and the solution evaporated to dryness under reduced pressure to give the monohydrochloride as colourless microcrystals m.p. 298°–304°C.

EXAMPLE 33

2-(2-benzimidazolyl)amino-2-(4-methylimidazoline)

2-Benzimidazolylcarbamonitrile (10.0 g, 0.063 mol) and 1-2-diaminopropane (22 ml, 19.2g. 0.189 mol) were heated under reflux in amyl alcohol (100 ml) for 5 hours. The reaction mixture was evaporated in vacuo and the resulting oil triturated with a little amyl alcohol. The crystalline precipitate was filtered washed with amyl alcohol and dried (7.37 g). Recrystallisation from amyl alcohol gave 2-(2-benzimidazolyl)amino-2-(4-methylimidazoline) (3.54 g; 26%) as off-white microcrystals m.p. 180°–182°C.

EXAMPLE 34

2-(2-benzimidazolyl)amino-2-(1-acetylimidazoline)

2-(2-Benzimidazolyl)amino-2-imidazoline(2.01 g, 0.01 mol) and acetic anhydride (1.02 g, 0.01 mol) in dimethylformamide (15 ml) were warmed on a water bath for 2 hours then allowed to stand overnight. Dilution to 100 ml with water gave 2-(2-benzimidazolyl)amino-2-(1-acetylimidazoline (1.59 g) as colourless microcrystals m.p. 260°–262°C.

EXAMPLE 35

Copper complex of 2-(2-benzimidazolyl)amino2-imidazoline

A solution of cupric sulphate pentahydrate (1.0g) in water (4 ml) was added to a solution of 2-(2-benzimidazolyl)amino-2-imidazoline (2.01 g, 0.01 mol) in water (20 ml) containing 5N sulphuric acid (4 ml) at 80°C. The green solution was cooled and diluted with an equal volume of ethanol to give a gelatinous precipitate which was filtered and dried in vacuo at 80°C to give pale green crystals (1.1g) with composition $Cu(C_{10}H_{11}N_5 \cdot 2H_2O)SO_4$.

EXAMPLE 36

2-(5,6-dimethylbenzimidazolyl)amino-2-imidazoline 5,6-Dimethylbenzimidazolylcarbamonitrile (10.0 g, 0.054 mol) was heated under reflux with excess ethylenediamine (11 ml) in amyl alcohol (100 ml) for 4 hours. The cooled reaction mixture was evaporated under reduced pressure and the resulting oil triturated with a little amyl alcohol. The crystalline precipitate was filtered, washed with a little amyl alcohol and dried in vacuo to yield 2-(5,6-dimethylbenzimidazolyl)amino-2-imidazoline (6.26 g, 51%) as colourless microcrystals m.p. 266°C.

The free base was dissolved in 5N hydrochloric acid and the solution evaporated under reduced pressure. Recrystallisation of the resulting solid twice from ethanol/ether gave the dihydrochloride hemi hydrate as colourless microcrystals m.p. 266°C (after drying for 5 hours under vacuum at 55°C).

EXAMPLES 37–39

The following compounds were prepared in a manner analogous to that described in Example 2.

| Compound | % Yield | Description | mpt |
| --- | --- | --- | --- |
| 2-Guanidino-4,6-dichlorobenzimidazole | 41 | light brown microcrystals | 264–5°C |
| 2-Guanidino-5-t-butylbenzimidazole (as monohydrated HCl salt) | 43 | light brown crystals | 226–8°C |
| | — | colourless microcrystals | 180–182°C |
| 2-Guanidino-5,6-dichlorobenzimidazole as the dihydrochloride hemihydrate | 10 | pink microcrystals | 305–320°C |

EXAMPLE 40

2-guanidino-5-benzyloxybenzimidazole

4-Benzyloxy-2-nitroacetanilide was prepared by the reaction of nitric acid and acetic acid on 4-benzyloxyacetanilide. Hydrolysis of the amide of refluxing methanol containing some sodium methoxide yielded 4-benzyloxy-2nitroaniline (m.p. 139°–141°C) which was -nitroaniline using a boiling solution of sodium dithionite in methanolic aqueous potassium hydroxide to give on separation 4-benzyloxy-ophenyldiamine as off-white microcrystals (m.p. 64°C) which on treatment with dry ethanolic hydrogen chloride gave pink microcrystals of the dihydrochloride (m.p. 200°–202°C). Reaction of 4-benzyloxy-o-phenyldiamine dihydrochloride and cyanoguanidine as in Example 2 yielded a mixed product (12.89g) when basified with 40% sodium hydroxide solution. Treatment with chloroform gave an insoluble residue (7.54g) m.p. 204°–209°C which was recrystalised from aqueous methanol to give 2-guanidino-5-benzyloxybenzimidazole (457g) as light brown microcrystals m.p. 224°–227°C.

EXAMPLE 41:

5-t-butyl-2-benzimidazolylcarbamonitrile

Reaction of 2-guanidino-5-t-butylbenzimidazole and nitrous acid as described in Example 10 yielded 5-t-butyl-2-benzimidazolylcarbamitrile (26%) as light-brown microcrystals, m.p, 277°C. (ex.methanol).

EXAMPLE 42

2-(5-acetylaminobenzimidazolyl) amino-2-imidazoline

A mixture of 2-(5-aminobenzimidazolyl) amino-2-imidazoline (0.48g, 0.0022 mol) and acetic anhydride (0.0022 mol) in ethanol (20 ml) was heated under reflux for 2 hours. The cooled reaction mixture was evaporated in vacuo and the resulting solid dissolved in methanol. Treatment with dry hydrogen chloride gas followed by ethyl acetate gave brown microcrystals (0.33 g). Recrystallisation from methanol/ethyl acetate gave a poor recovery of slightly hydroscopic 2-(5-acetylamino-2-benzimidazolyl) amino-2-imidazoline (50 mg) as colourless microcrystals m.p. 294°C (with shrinking).

EXAMPLES 43 and 44

2-t-Butyl-2-benzimidazolyl) amino-2-imidazoline (yield 30% of free base as colourless microcrystals, m.p. 278°–280°C., ex aqueous ethanol, hydrochloride salt m.p. 202–208°C.) and 2-(4,5-dimethyl-2-benzimidazolyl) amino-2-imidazoline (yield 30% of hydrochloride salt as colourless microcrystals, m.p. 199°–204°C) were prepared from the corresponding carbamonitriles as described in Example 17.

EXAMPLE 45

2-(5,6-dichloro-2-benzimidazolyl) amino-2-imidazoline 2-(5,6-Dichloro-2-benzimidazolyl)-guanidine dihydrochloride hemi-hydrate (150 mg) and ethylene diamine (60 mg) were heated under reflux for 21 hours in amyl alcohol (3ml). The reaction mixture was evaporated to dryness in vacuo to yield a brown gum. This was triturated with water to give orange crystals (170 mg) m.p. 224°–227°C. N.m.r. shows this to be a mixture (4:1) of the guanidine and imidazoline. A solution of the free base in ethanol when treated with ethanolic hydrogen chloride gave a mixture of hydrochloride salts. N.m.r. indicates this is about a 3:1 mixture of starting material and 2-(5,6-dichloro-2-benzimidazolyl) amino-2-imidazoline as their hydrochloride salts. Fractional crystallisation yielded a sample of pure product identical with an authentic sample prepared by chlorination of 2-benzimidazolylamino-2-imidazoline.

EXAMPLE 46

2-(5,6-dichloro-2-benzimidazolyl) amino-2-imidazoline 2-(2-Benzimidazolyl) amino-2-imidazoline dihydrochloride (13.7g, 0.05 mol) was dissolved in concentrated hydrochloric acid (100 ml) and water (100 ml). The solution was stirred and heated to 70°C. A 10% solution of hydrogen peroxide (27 ml) was added dropwise over 10 minutes resulting in precipitation of a white solid. Water (100 ml) was added to cool the reaction mixture to 60°C. A further quantity of 10% hydrogen peroxide (10.5 ml; 10% excess in all) was added. The reaction mixture was heated to 80°C for 15 minutes, and filtered whilst hot to give a solid m.p. 265°–272°C. The filtrate was cooled to give more solid m.p. 285°–292°C. Finally evaporation of the mother liquors in vacuo yielded a third quantity. All 3 solids were combined and recrystallised twice from water to yield 2-(5,6-Dichloro-2-benzimidazolyl) amino-2-imidazoline hydrochloride (7.86g; 53%) as colourless microcrystals m.p. 279° –281°C.

EXAMPLE 47

2-(4,5,6-trichloro-2-benzimidazolyl) amino-2-imidazoline and 2-(4,5,6,7-tetrachloro-2-BENZIMIDAZOLYL) AMINO-2-imidazoline 2-(2-Benzimidazolyl) amino-2-imidazoline dihydrochloride (27.4g, 0.10 mol) was dissolved in concentrated hydrochloric acid (300 ml). The solution was stirred and heated to 80°C. A 15% solution of hydrogen peroxide (68 ml) was added dropwise to the stirred solution, the temperature was allowed to rise to 100°C resulting in precipitation of a white solid from dimethylformamide and/or water to give predominately 2-(4,5,6,7-tetrachloro-2-benzimidazolyl) amino-2-imidazoline as colourless microcrystals m.p. 310°C together with a lower yield of 2-(4,5,6-trichloro-2-benzimidazolyl) amino-2-imidzoline as colourless microcrystals m.p. 324°–326°C in addition to 2-(5,6-dichloro-2-benzimidazolyl) amino-2-imidazoline monohydrochloride m.p. 279–281°C.

EXAMPLE 48

Pharmacology a. Metacortacoid hypertension was induced by the method of Green et al. [Amer. J. Physiol., 170, 94 (1952)]. All compounds were suspended in methylcellulose and administered orally to the metacorticoid hypertensive rats at a dose of 100mg/kg. The blood pressure was measured indirectly in conscious, restrained rats by the method of Friedman et al. [Proc. Soc. Exper. Biol. Med., 70, 670 (1949)]. The following results were obtained for compounds of the formula:

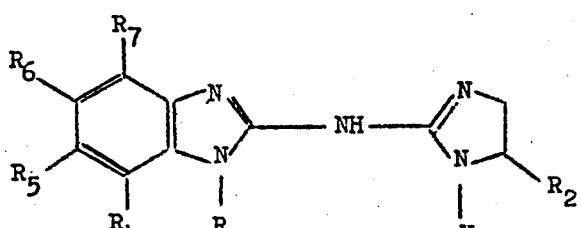

| Compound | | | | | | % Fall in systalic blood pressure after 4 hours |
|---|---|---|---|---|---|---|
| $R_3$ | $R_5$ | $R_6$ | $R_7$ | $R_2$ | | |
| H | H | H | H | H | ** | 21 |
| $CH_3$ | H | H | H | H | * | 10 |
| H | H | $CH_3$ | H | H | ** | 25 |
| H | H | $CH_3O$ | H | H | ** | 35 |
| H | H | Cl | H | H | ** | 37 |

—Continued

| Compound | | | | | | % Fall in systalic blood pressure after 4 hours |
|---|---|---|---|---|---|---|
| $R_3$ | $R_5$ | $R_6$ | $R_7$ | $R_2$ | | |
| $C_6H_5CH_2$ | H | H | H | H | | 6 |
| H | H | $NO_2$ | H | H | | 11 |
| H | H | H | H | $CH_3$ | | 13 |
| H | H | $NH_2$ | H | H | ** | 11 |
| H | $CH_3$ | $CH_3$ | H | H | ** | 6 |
| H | H | H | $CH_3$ | H | ** | 19 |
| H | H | Br | H | H | * | 22 |
| H | Cl | Cl | H | H | ** | 35 |
| H | Br | Br | H | H | * | 23 |
| H | H | $SO_3H$ | H | H | | 6 |
| H | Cl | Cl | Cl | H | | 16 |
| H | H | OH | H | H | | 13 |

\* = Tested as hydrochloride salt
\*\* = Tested as dihydrochloride salt b. Using the test methods described in (a), the following dose/time responses were determined:

| Compound | 100 mgs/kg | | | 10 mgs/kg | | |
|---|---|---|---|---|---|---|
| | 4 hrs | 6 hrs | 24 hrs | 4 hrs | 6 hrs | 24 hrs |
| 2-(2-benzimidazolyl)amino-2-imidazoline dihydrochloride | 21 | 32 | 2 | 12 | 14 | 11 |
| 2-(5-bromo-2-benzimidazolyl) amino-2-imidazoline hydrochloride | 22 | 36 | 26 | 23 | 19 | 7 |
| 2-(5-methoxy-2-benzimidazolyl) amino-2-imidazoline dihydrochloride | 35 | 36 | 12 | 19 | 12 | 13 |
| 2-(5,6-dichloro-2-benzimidazolyl)amino-2-imidazoline hydrochloride | 35 | 43 | 24 | 36 | 33 | 14 | c. Using the test methods described in (a), the following additional information on 2-(5,6-dichloro-2-benzimidazolyl) amino-2-imidazoline hydrochloride was obtained:

| Dose in mg/kg | % Fall after no. of hours | | |
|---|---|---|---|
| | 4 | 6 | 24 |
| 100 | 35 | 43 | 24 |
| 10 | 36 | 33 | 14 |
| 3 | 22 | 21 | 19 |
| 0.3 | 17 | 30 | 22 |
| 0.1 | 14 | 12 | 12 | d. The following anti-hypertensive agents which are not compounds of the invention were tested by the methods of (a):

| Compound | Dose (mg/kg) | % Fall after no. of hours | | |
|---|---|---|---|---|
| | | 4 | 6 | 24 |
| 2-Acetylamino-5,6-dimethyl benzimidazole) HCl | 100 | 6 | 14 | 5 |
| 2-(2-Benzolthiazolyl) amino-2-imidazoline HCl. ½ $H_2O$ | 100 | 8 | NT | 4 |
| -Methyldopa | 100 | 29 | 28 | 9 |
| L-Methyldopa | 30 | 16 | 9 | −4 |
| Guanethidine | 100 | 34 | 30 | 31 |
| Guanethidine | 10 | 10 | 14 | 5 |
| Reserpine | 3 | 32 | 37 | 23 |
| Reserpine | 0.3 | 11 | 9 | 8 |
| Clonidine | 0.1 | 13 | NT | −4 |
| Clonidine | 0.01 | 5 | NT | −8 |

NT means that no test was carried out.

The compounds of the invention do not exhibit side effects such as the pressor activity sometimes associated with guanethidine (1-guanidino-2-heptamethyleneaminoethane), the periferal vasoconstrictor effects sometimes associated with clonidine (2,6-dichlorophenyl-2-aminoimidazoline), the tranquilliser and depressive effects sometimes associated with reserpine or the drowsiness and diarrhea sometimes associated with L-methyldopa.

e. The effect of compounds of the invention on the blood pressure of conscious normotensive rats was determined by recording in a direct manner the blood pressure in unrestricted animals by means of an indwelling catheter [weeks et al., Proc. soc. exp. Biol., N.Y. 104, 646 (1960)].

No significant change was observed in the blood pressure of any of the rats used in the test indicating that the compounds studied have no effect on the blood pressure of normotensive animals.

f. When tested on mice for central nervous system activity by standard methods, oral doses of 100 mg/kg of 2-(5,6-dichlorobenzimidazolyl)amino-2-imidazoline showed no effect on observable activity, hexobarbitone potentiation tests, antielectric shock convulsion tests or anti-clonidine induced fighting tests.

g. When administered intravenously in ascending doses to anaesthetised normotensive dogs and cats no specific direct effects could be observed to occur with 2-(5,6-dichlorobenzimidazolyl) amino-2-imidazoline and in particular no blocking effects on the autonomic nervous system were observed.

When tested under these conditions 1μg/kd of clonidine caused a rise in blood pressure which at 30μg/kg was pronounced and fairly prolonged and followed by prolonged hypotension. Under the same conditions infusion of L-methyldopa at 20mg/kg and above caused prolonged hypotension and guanethidine at 1mg/kg and above caused pronounced hypertension accompanied by blocking of the functioning of sympathetic nerves.

h. When tested for anti-inflammatory activity by the inhibition of oedema evoked by injection of carrageenin into the rats food (Winter et al., J.Pharm. exp. ther., 141, 369 (1963) at a dose of 100 mg/kg per os 2-(5-chloro-2-benzimidazolyl) amino-2-imidazoline produced a 31% inhibition of oedema and the corresponding 5-nitro compound produced a 37% inhibition of oedema. (cf. 44% inhibition caused by the currently widely used but ulcer-forming indomethacin).

i. The analgesic activity of 2-(5-nitro-2-benzimidazolyl)amino-2-imidazoline was demonstrated by its ability to inhibit 50% of the phenylquinone induced writhing when given to mice subcutaneously at a dose of 50 mg/kg under the test method of Siegmend et al., Proc. soc. exp. Biol., N.Y. 95, 729–731 (1957).

EXAMPLE 49

2-(5,6-Dichlorobenzimidazoleyi) amino-2-imidazoline 2-(5-Choro-2-benzimidazolyl) amino-2-imidazoline dihydrochloride (3.1g, 0.01 mol) in concentrated hydrochloric acid (25 ml) was treated with hydrogen peroxide (10%, 3.4ml) then heated to 80°C, maintained at this temperature for 15 minutes and then allowed to cool to room temperature. Recrystalisation of the resulting precipitate from water gave 2-(5,6-dichlorobenzimidazolyl) amino-2-imidazoline hydrochloride (0.46g, 15%) m.p. 279°–281°C.

EXAMPLE 50

Pharmacology 48a

Using the method described in example 48a the following results were obtained for compounds of the formula:

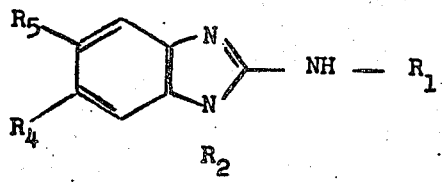

| $R_1$ | Compound $R_2$ | $R_4$ | $R_5$ | % Fall in systalic blood pressure after 4 hrs. at 100 mg/kg. |
|---|---|---|---|---|
| CN | H | H | H | 5 |
| CN | Na | H | H | 15 |
| CN | $CH_3$ | H | H | 25 |
| CN | H | H | $CH_3$ | 26 |
| CN | H | H | Cl | 32 |
| CN | H | H | $OCH_3$ | 11 |
| CN | H | $CH_3$ | $CH_3$ | 28 |
| $C(NH)NH_2$ | H | H | H | 14 |
| $C(NH)NH_2$ | $CH_3$ | H | H | 16 |
| $C(NH)NH_2$ | H | H | Cl | 15 |
| $C(NH)NH_2$ | $CH_2C_6H_5$ | H | H | 11 |
| $C(NH)NH_2$ | H | Cl | Cl | 10 |

21
—Continued

| | Compound | | | % Fall in systolic |
|---|---|---|---|---|
| $R_1$ | $R_2$ | $R_4$ | $R_5$ | blood pressure after 4 hrs. at 100 mg/kg |
| CN | H | H | H | 5 |
| CN | Na | H | H | 15 |
| CN | $CH_3$ | H | H | 25 |
| CN | H | H | $CH_3$ | 26 |
| CN | H | H | Cl | 32 |
| CN | H | H | $OCH_3$ | 11 |
| CN | H | $CH_3$ | $CH_3$ | 28 |
| $C(NH)NH_2$ | H | H | H | 14 |
| $C(NH)NH_2$ | $CH_3$ | H | H | 16 |
| $C(NH)NH_2$ | H | H | Cl | 15 |
| $C(NH)NH_2$ | $CH_2C_6H_5$ | H | H | 11 |
| $C(NH)NH_2$ | H | Cl | Cl | 10 |

EXAMPLE 51

5-fluoro-2-guanidinobenzimidazole

4-Fluoro-o-phenylenediamine (10.40g) was reacted with cyanoguanidine (6.95g) in a manner analagous to that described in Example 3 to yield a brown crystaline precipitate (11.61g) which on crystalisation from water yielded 5-fluoro-2-quanidinobenzimidazole (9.17g) m.p. 217°–218°C as brown needles.

EXAMPLE 52

5-fluorobenzimidazole - 2 - carbamonitrile

5-Fluoro-2-quanidinobenzimidazole (4.64g) was dissolved in a mixture of cold water (20 ml) and 5N hydrochloric acid (14.20ml). Treatment with sodium nitrite (1.64g) as in Example 7 caused the gradual precipitation of a brown solid which was filtered off. Treatment of the filtrate with sodium nitrite (1.00g) yielded after 16 hrs a second crop (1.46g) of brown solid. The combined solids were recrystalised from aqueous dimethylformamide to yield buff microcrystals of 5-fluorobenzimidazole-2-carbamonitrile (2.55g., 61%) m.p. 277°–286°C.

EXAMPLE 53

4,6-dichloro-2-Guanidinobenzimidazole 3,5-Dichloro-o-phenylenediamine (5.20g) was reacted with cyanoguanidine as described in Example 52 to yield a brown solid (4.78) which on recrystalisation from aqueous ethanol gave 4,6-dichloro-2-guanidinobenzimidazole (3.09g) as light brown microcrystals, m.p. 264°–265°C.

EXAMPLE 54

5-trifluoromethyl-2-guanidinobenzimidazole

4-Trifluoromethyl -o- phenylenediamine (25.46g) and cyanoguanidine (12.40g) were reacted together in a manner analogous to that of Example 2 to yield 5-Trifluoromethyl-2-guanidinobenzimidazole is a red gummy solid which when dissolved in 5N hydrochloric acid and evaporated to dryness yielded the dihydrochloride (25.01g) as a brown solid, m.p. 206°–209°C.

Example 55

5-trifluoromethyl-2-benzimidazolyl carbamonitrile

Treatment of 5-trifluoromethyl-2guanidinobenzimidazol dihydrochloride (18.89g) with sodium nitrite in a manner analogous to that described in Example 52 yielded the desired product in impure state. Column chromatography over silicagel using a mixture of methanol and chloroform as eluent yielded 5-trifluoromethyl-2-benzimidazolylcarbamonitril (3.80g) as a yellow powder. Recrystalisation from aqueous dimethylformamide gave cream microcrystals m.p. 237°–240°C (de comp)

What is claimed is:

1. A pharmaceutical composition for the treatment of hypertension comprising an anti-hypertensively effective amount of a compound of the formula:

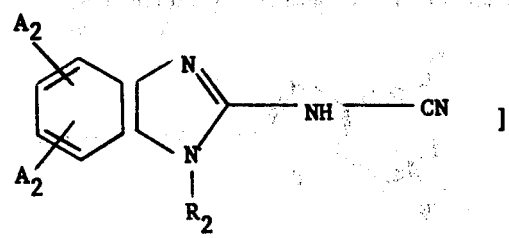

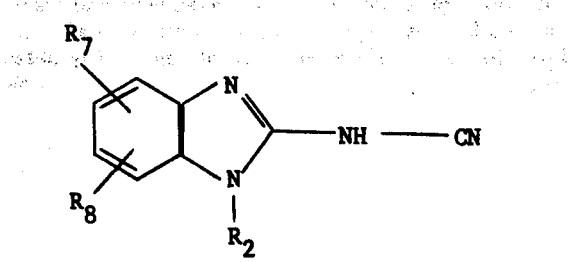

or a pharmaceutically acceptable salt thereof wherein $R_2$ is hydrogen or alkyl of 1–7 carbon atoms and each of $R_7$ and $R_8$ is hydrogen, halogen, lower alkyl or lower alkoxy together with a pharmaceutically acceptable carrier.

2. An anti-hypertensive composition according to claim 1 wherein $R_2$ is hydrogen or methyl and each of $R_7$ and $R_8$ is hydrogen, chlorine, bromine or methyl.

3. A pharmaceutical composition according to claim 1 wherein the anti-hypertensive compound is 2-benzimidazolyl carbamonitrile.

4. A pharmaceutical composition according to claim 1 wherein the anti-hypertensive compound is 1-methyl-2-benzimidazolylcarbamonitrile.

5. A pharmaceutical composition according to claim 1 wherein the anti-hypertensive compound is 5-methyl-2-benzimidazolylcarbamonitrile.

6. A pharmaceutical composition according to claim 1 wherein the anti-hypertensive compound is 5-chloro-2-benzimidazolylcarbamonitrile.

7. A pharmaceutical composition according to claim 1 wherein the anti-hypertensive compound is 5-methoxy-2-benzimidazolylcarbamonitrile.

8. A pharmaceutical composition according to claim 1 wherein the anti-hypertensive compound is 5,6-dimethyl-2-benzimidazolylcarbamonitrile.

9. A pharmaceutical composition according to claim 1 wherein the anti-hypertensive compound is 4-methyl-2-benzimidazolylcarbamonitrile.

10. A pharmaceutical composition according to claim 1 wherein the anti-hypertensive compound is 4,5-dimethyl-2-benzimidazolylcarbamonitrile.

11. A pharmaceutical composition according to claim 1 wherein the anti-hypertensive compound is 5-fluorobenzimidazole-2-carbamonitrile.

12. A pharmaceutical composition according to claim 1 wherein the anti-hypertensive compound is 5-trifluoromethyl-2-benzimidazolylcarbamonitrile.

13. A method of treatment of hypertension in mammals which comprises the administration to said mammal of an anti-hypertensively effective amount of a composition comprising an anti-hypertensively effective amount of a compound of the formula:

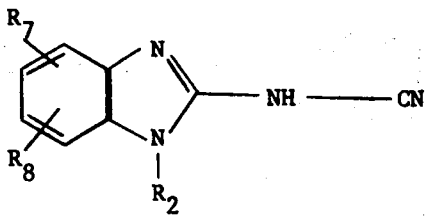

or a pharmaceutically acceptable salt thereof wherein $R_2$ is hydrogen or alkyl of 1–7 carbon atoms and each of $R_7$ and $R_8$ is hydrogen, halogen, lower alkyl or lower alkoxy together with a pharmaceutically acceptable carrier.

14. A method of treatment of hypertension in a mammal which comprises the administration to said mammal of an anti-hypertensively effective amount of a composition comprising an anti-hypertensively effective amount of a compound of the formula:

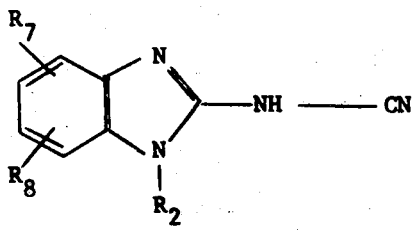

or a pharmaceutically acceptable salt thereof wherein $R_2$ is hydrogen or methyl and each of $R_7$ and $R_8$ is hydrogen, chlorine, bromine or methyl together with a pharmaceutically acceptable carrier, wherein the composition is in oral dosage form containing from 5 to 500 mgs of anti-hypertensive compound.

* * * * *

UNITED STATES PATENT AND TRADEMARK OFFICE
CERTIFICATE OF CORRECTION

PATENT NO. : 3,935,314
DATED : January 27, 1976
INVENTOR(S) : Eric Alfred Watts

It is certified that error appears in the above—identified patent and that said Letters Patent are hereby corrected as shown below:

Column 22, lines 10-30   In claim 1, the structural formulas now appearing as

[ 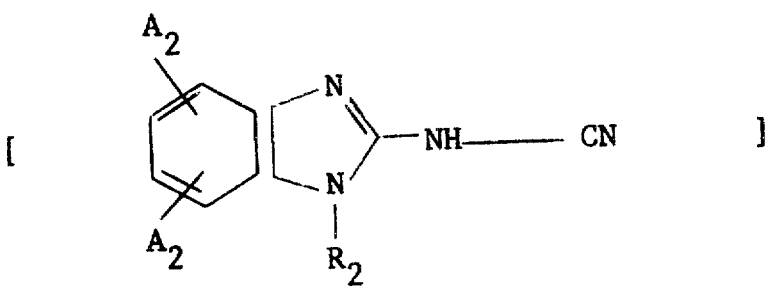 ]

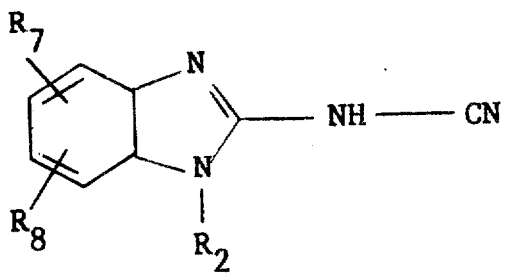

should read

-- 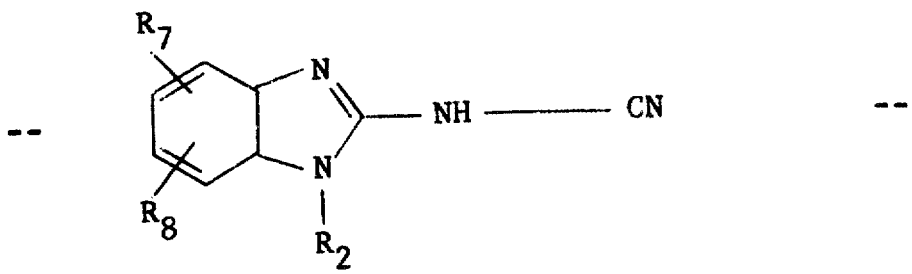 --

Signed and Sealed this twenty-seventh Day of April 1976

[SEAL]

Attest:

RUTH C. MASON
Attesting Officer

C. MARSHALL DANN
Commissioner of Patents and Trademarks